United States Patent [19]

Oshima et al.

[11] Patent Number: 4,837,147

[45] Date of Patent: Jun. 6, 1989

[54] PHO81 PROMOTOR OF *SACCHAROMYCES CEREVISIAE* AND USE THEREOF FOR HETEROLOGOUS GENE EXPRESSION

[75] Inventors: Yasuji Oshima, Takatsuki; Hiroyuki Araki; Yoshinobu Kaneko, both of Suita, all of Japan

[73] Assignee: Takeda Chemical Industries, Ltd., Osaka, Japan

[21] Appl. No.: 896,176

[22] Filed: Aug. 13, 1986

[30] Foreign Application Priority Data

Aug. 20, 1985 [JP] Japan .................................. 60-180984

[51] Int. Cl.$^4$ ...................... C12P 21/00; C12P 21/02; C12N 15/00; C07H 15/12

[52] U.S. Cl. ........................................ 435/68; 435/70; 435/91; 435/172.3; 435/255; 435/256; 435/320; 536/27; 935/28; 935/37; 935/43; 935/56; 935/60; 935/65; 935/64

[58] Field of Search ...................... 435/68, 172.3, 255, 435/320, 256, 91, 70, 194; 536/27; 935/28, 37, 43, 56, 60, 65, 69

[56] References Cited

FOREIGN PATENT DOCUMENTS 190560 10/1983 European Pat. Off. ......... 435/172.3

OTHER PUBLICATIONS

Kramer et al., *Proc. Natl. Acad. Sci.* vol. 81 (2) pp. 367-370 "Regulated expression of a human interferon gene on yeast: control by phosphate concentration or temperature".
Valenzuela et al., *Nature* vol. 298 Jul. 22 1982 pp. 317-350 "Synthesis and Assembly of hepatitis B Virus Surface Antigen particles on yeast."
Lemire et al., *Mol Cell Biol.* vol. 5 (8) Aug. 1985 pp. 2131-2141 "Regulation of repressible acid phosphatase gene transcription in Saccharomyces cerevisiae".
Toh-e et al., (including Oshima) *Hakko Kogaku Kaishi,* vol. 61 (1) pp. 19-30 1983.
MGG. volume 162, pp. 139-149 (1978).
Oshima et al.; the Molecular Biology of the Yeast Saccharomyces, Metabolism and Gene Expression pp. 159-180(1982), Cold Spring Harbor Lab.
Kaneko et al.; Molecular and Cellular Biology 5, 248-252, Jan. (1985).
Oshima et al.; Yeast Genetics and Molecular Biology News Japan No. 18, pp. 37 Sep. 18-20, 1985.
Oshima et al.; the 57th Annual Meeting of the Genetics Society of Japan, p. 51 (C 09) Oct. 13-15, 1985.
Oshima et al.; the Japanese Journal of Genetics vol. 60 p. 644 No. 217 Dec. (1985).

*Primary Examiner*—Robin Teskin
*Attorney, Agent, or Firm*—Ernest V. Linek; David G. Conlin

[57] ABSTRACT

The present invention relates to a DNA fragment having a promoter activity of PHO81 gene regulating the production of phosphatase, and which is obtainable from *Saccharomyces cerevisiae*.; a DNA fragment bearing a structural gene downstream from the above PHO81 promoter; a transformant containing a DNA fragment bearing the above PHO81 promoter; a transformant containing a DNA fragment bearing the above PHO81 promoter and a structural gene downstream from the PHO81 promoter; and a process for obtaining a gene product which includes culturing a transformant containing a DNA fragment bearing the above PHO81 promoter and a structural gene located downstream therefrom in a suitable medium until the gene product is formed and recovering the gene product from the culture. Pharmacologically important proteinous materials may be efficiently produced with the use of the above-described novel and potent promoter obtained from yeast which is a eukaryotic microorganism.

14 Claims, 5 Drawing Sheets

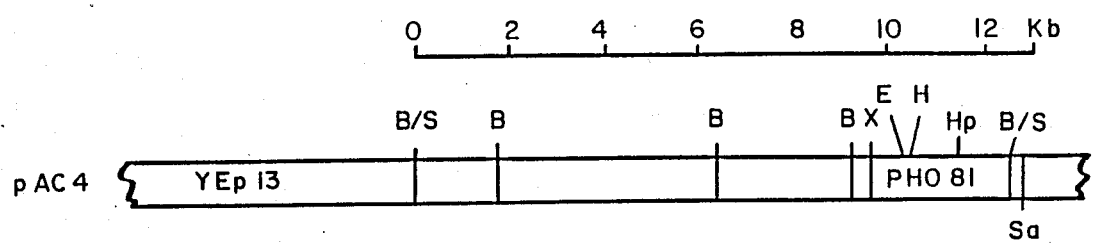
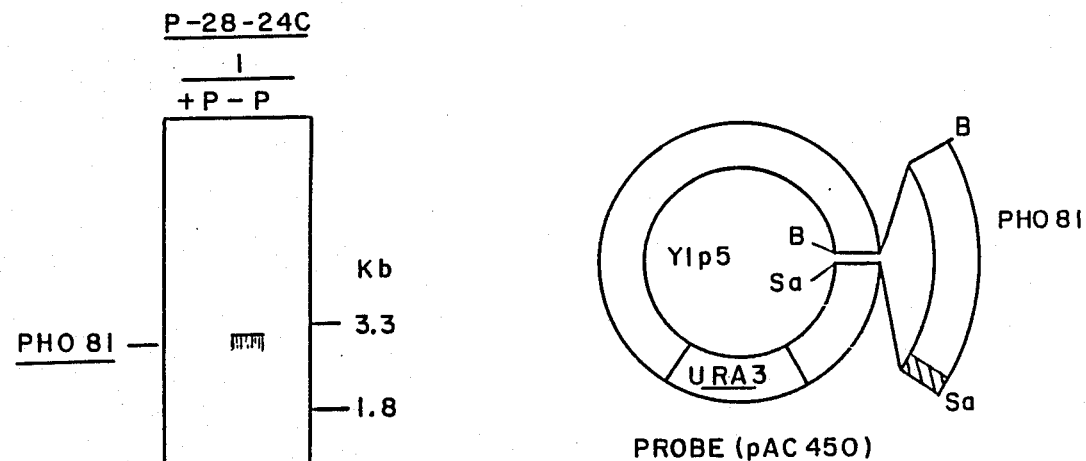
B. BamHI
E. EcoRI
H. HindIII
Hp. HpaI
X. XhoI
B/S. BamHI/Sau3A
Sa. Sa/L
FIG. 3

Fig. 5

```
             -500
TCCCAACGAAATTGATGGGTTTAATAAATGGACGCCCATTTTTTACGCTG
AGGGTTGCTTTAACTACCCAAATTATTTACCTGCGGGTAAAAAATGCGAC

-450
TTCGTTCAGGTCATTCTGAAGTTATTACTGAATTATTGAAACATAATGCA
AAGCAAGTCCAGTAAGACTTCAATAATGACTTAATAACTTTGTATTACGT

-400          HaeIII
CGTCTGGATATTGAAGATGACAACGGCCATTCGCCACTTTTTTACGCCTT
GCAGACCTATAACTTCTACTGTTGCCGGTAAGCGGTGAAAAAATGCGGAA

-350
ATGGGAGGACCACGTTGATGTTTTGAATGCACTTTTACAAGAACCATTAA
TACCCTCCTGGTGCAACTACAAAACTTACGTGAAAATGTTCTTGGTAATT

-300                           RsaI
ATTTGCCACCGCACCCCGAATGAAATGAATTCGCAGTCTAGTACGCAACG
TAAACGGTGGCGTGGGGCTTACTTTACTTAAGCGTCAGATCATGCGTTGC

-250
CCTTAATACAATAGATTTAACCCCAAATGATGACAAATTTGATTTAGACA
GGAATTATGTTATCTAAATTGGGGTTTACTACTGTTTAAACTAAATCTGT

-200
TTCAAGATAGCATTCCGGATTTTGCTTTACCACCGCCAATCATTCCACTA
AAGTTCTATCGTAAGGCCTAAAACGAAATGGTGGCGGTTAGTAAGGTGAT

-150
AGGAAATATGGTCATAATTTTTTGGAGAAAAAATTTTCATCAAATTAAA
TCCTTTATACCAGTATTAAAAAACCTCTTTTTTAAAAGTAGTTTAATTT

-100 XhoI                       TATA BOX
GTTAAGGCCAGGTCTCGAGTCTATCAAGTTGATTTAGGATAACGGCATTA
CAATTCCGGTCCAGAGCTCAGATAGTTCAACTAAATCCTATTGCCGTAAT

-50 BstNI
TTATGTCATCATCACCAGGCAGAATTACTTTATCCTCTAACTTACCTGAA
AATACAGTAGTAGTGGTCCGTCTTAATGAAATAGGAGATTGAATGGACTT

AccII-1+1
ATAATACCGCGAAATGTTATTTTACCTGTTAGATTTGGCGAAATTAATAA
TATTATGGCGCTTTACAATAAAATGGACAATCTAAACCGCTTTAATTATT

+50
CTTTTGTAGATATCAGTGAAACGAATGATGAAGAAGATGATGATGAAATT
GAAAACATCTATAGTCACTTTGCTTACTACTTCTTCTACTACTACTTTAA

Sau3A +100
AGTGAAGATCATGATGATGGAGAGATAATTTTCCAAGTAGATTCAATCGA
TCACTTCTAGTACTACTACCTCTCTATTAAAAGGTTCATCTAAGTTAGCT

+150
CGATTTTTCAATGGATTTCGAGATATTTCCTTCATTTGGCACAAGGA
GCTAAAAAGTTACCTAAAGCTCTATAAAGGAAGTAAACCGTGTTCCT
```

Fig. 9-1

```
             10        20        30        40        50
    TCCCAACGAAATTGATGGGTTTAATAAATGGACGCCCATTTTTTACGCTG
    AGGGTTGCTTTAACTACCCAAATTATTTACCTGCGGGTAAAAAATGCGAC 60        70        80        90       100
    TTCGTTCAGGTCATTCTGAAGTTATTACTGAATTATTGAAACATAATGCA
    AAGCAAGTCCAGTAAGACTTCAATAATGACTTAATAACTTTGTATTACGT 110       120       130       140       150
    CGTCTGGATATTGAAGATGACAACGGCCATTCGCCACTTTTTTACGCCTT
    GCAGACCTATAACTTCTACTGTTGCCGGTAAGCGGTGAAAAAATGCGGAA 160       170       180       190       200
    ATGGGAGGACCACGTTGATGTTTTGAATGCACTTTTACAAGAACCATTAA
    TACCCTCCTGGTGCAACTACAAAACTTACGTGAAAATGTTCTTGGTAATT 210       220       230       240       250
    ATTTGCCACCGCACCCCGAATGAAATGAATTCGCAGTCTAGTACGCAACG
    TAAACGGTGGCGTGGGGCTTACTTTACTTAAGCGTCAGATCATGCGTTGC 260       270       280       290       300
    CCTTAATACAATAGATTTAACCCCAAATGATGACAAATTTGATTTAGACA
    GGAATTATGTTATCTAAATTGGGGTTTACTACTGTTTAAACTAAATCTGT 310       320       330       340       350
    TTCAAGATAGCATTCCGGATTTTGCTTTACCACCGCCAATCATTCCACTA
    AAGTTCTATCGTAAGGCCTAAAACGAAATGGTGGCGGTTAGTAAGGTGAT 360       370       380       390       400
    AGGAAATATGGTCATAATTTTTTGGAGAAAAAAATTTTCATCAAATTAAA
    TCCTTTATACCAGTATTAAAAAACCTCTTTTTTTAAAAGTAGTTTAATTT 410       420       430       440       450
    GTTAAGGCCAGGTCTCGAGTCTATCAAGTTGATTTAGGATAACGGCATTA
    CAATTCCGGTCCAGAGCTCAGATAGTTCAACTAAATCCTATTGCCGTAAT 460       470       480       490       500
    TTATGTCATCATCACCAGGCAGAATTACTTTATCCTCTAACTTACCTGAA
    AATACAGTAGTAGTGGTCCGTCTTAATGAAATAGGAGATTGAATGGACTT 510       520       530       540       550
    ATAATACCGCGAAATGTTATTTTACCTGTTAGATTTGGCGAAATTAATAA
    TATTATGGCGCTTTACAATAAAATGGACAATCTAAACCGCTTTAATTATT
```

Fig. 9-2

```
          560        570        580        590        600
CTTTTGTAGATATCAGTGAAACGAATGATGAAGAAGATGATGATGAAATT
GAAAACATCTATAGTCACTTTGCTTACTACTTCTTCTACTACTTTAA 610        620        630        640        650
AGTGAAGATCATGATGATGGAGAGATAATTTTCCAAGTAGATTCAATCGA
TCACTTCTAGTACTACTACCTCTCTATTAAAAGGTTCATCTAAGTTAGCT 660        670        680        690        700
CGATTTTTCAATGGATTTCGAGATATTTCCTTCATTTGGCACAAGGATAA
GCTAAAAAGTTACCTAAAGCTCTATAAAGGAAGTAAACCGTGTTCCTATT 710        720        730        740        750
TTGCCAAAACAACGGCAATGCCATTCCTTTTCAAGAAAGTGGCAATAAAT
AACGGTTTTGTTGCCGTTACGGTAAGGAAAAGTTCTTTCACCGTTATTTA 760        770        780        790        800
AGTATTGCAACCATGAATTTACCCTTATTCCACACAAGGCTAAATAATAT
TCATAACGTTGGTACTTAAATGGGAATAAGGTGTGTTCCGATTTATTATA 810        820        830        840        850
TGGATCTCTCACTTTGGATTACCAAATTATTTTTCCTTATCCGGGAAATC
ACCTAGAGAGTGAAACCTAATGGTTTAATAAAAAGGAATAGGCCCTTTAG 860        870        880        890        900
CACTGAAAATCATAAAATATGAGCCGTATTGGAAACTTACAGGAAGTGAT
GTGACTTTTAGTATTTTATACTCGGCATAACCTTTGAATGTCCTTCACTA 910        920        930        940        950
TTAATGACCTCTAGTAAAGACGGTAATTTTGTTACTTCTTCATCGTTGAA
AATTACTGGAGATCATTTCTGCCATTAAAACAATGAAGAAGTAGCAACTT 960        970        980        990       1000
TGGCAGTTTTATTAGTGTATTAGTTTGCGCTCTGAATGATGAAACCATAG
ACCGTCAAAATAATCACATAATCAAACGCGAGACTTACTACTTTGGTATC 1010       1020       1030       1040       1050
TGGCTGCGCCAAAACCATGTGTTGAATTCAAAGGAGCGAAGATTCTGTTA
ACCGACGCGGTTTTGGTACACAACTTAAGTTTCCTCGCTTCTAAGACAAT 1060       1070       1080       1090       1100
AATGATTTAACGAAAGAACAATTGGAAAAAGTAGTGGATTATGACTTCGG
TTACTAAATTGCTTTCTTGTTAACCTTTTTCATCACCTAATACTGAAGCC
```

Fig.9-3

```
           1110      1120      1130      1140      1150
      TAAAATTGATGGAAGCTTCGATGAAGTAACATTGAAACAATACTTATCTT
      ATTTTAACTACCTTCGAAGCTACTTCATTGTAACTTTGTTATGAATAGAA 1160      1170      1180      1190      1200
      GCAGAGTGGTGCCTCTCAGAAGCCTACTAGAAGTTATTCCCGGGTCAGTC
      GCTCTCACCACGGAGAGTCTTCGGATGATCTTCAATAAGGGCCCAGTCAG 1210      1220      1230      1240      1250
      CAGCTGGTAATTCGTGTATATTTTCCTACAGATAAGGAAATTGACACAAT
      GTCGACCATTAAGCACATATAAAAGGATGTCTATTCCTTTAACTGTGTTA 1260      1270      1280      1290      1300
      TCCCATCAAAATATCGCCATTTATAAATATCAATCAGTTCATTGATAAGC
      AGGGTAGTTTTATAGCGGTAAATATTTATAGTTAGTCAAGTAACTATTCG 1310      1320      1330      1340      1350
      TTTTACTAATCATTTTCGAGCATGAACGTTTTTTGCGACGCAGCGGAAGT
      AAAATGATTAGTAAAAGCTCGTACTTGCAAAAAACGCTGCGTCGCCTTCA 1360      1370      1380      1390      1400
      TGGAGTATGCGCCAAATAGTTTTCAGTTCATGCGATTCCCAAGCTTGCTC
      ACCTCATACGCGGTTTATCAAAAGTCAAGTACGCTAAGGGTTCGAACGAG 1410      1420      1430      1440      1450
      GATCCTTAACTGGAAACAACCCAATTTTCCGGTTTTGTTGCAAATGAAAA
      CTAGGAATTGACCTTTGTTGGGTTAAAAGGCCAAAACAACGTTTACTTTT 1460      1470      1480      1490      1500
      ATCTACTCAGAGATTCAACCACAGGCAAATTTGTAGGTGATACTCCCAAT
      TAGATGAGTCTCTAAGTTGGTGTCCGTTTAAACATCCACTATGAGGGTTA 1510      1520      1530      1540      1550
      TGTTTAAAGGAACTGGCAGTAAATCCTCAAAAAATGTCGTATTTAAACAC
      ACAAATTTCCTTGACCGTCATTTAGGAGTTTTTTACAGCATAAATTTGTG 1560      1570      1580      1590      1600
      GGAACTAATAAACATACATACAATGGTTCAATTTGCTATGAACAATAATT
      CCTTGATTATTTGTATGTATGTTACCAAGTTAAACGATACTTGTTATTAA 1610      1620      1630      1640      1650
      TGTTAGGTGTAACGCTTCCATATGAAGTACTGAAGATATGCCCGTCGTTG
      ACAATCCACATTGCGAAGGTATACTTCATGACTTCTATACGGGCAGCAAC
```

Fig. 9-4

```
          1660       1670       1680       1690       1700
    GCTAGGATCATCAAACAAAACGGACTATTGTTGATTGCATCGGTCGGGGA
    CGATCCTAGTAGTTTGTTTTGCCTGATAACAACTAACGTAGCCAGCCCCT 1710       1720       1730       1740       1750
    AAATGACCAAATACCAGCTGATGGGGGTTACAGCGGGATCTACTACGCTT
    TTTACTGGTTTATGGTCGACTACCCCCAATGTCGCCCTAGATGATGCGAA 1760       1770       1780       1790       1800
    GTGAGTTACTTTTTGAGAATAATATTGATATGCAAAGTTCTCTAATATGT
    CACTCAATGAAAAACTCTTATTATAACTATACGTTTCAAGAGATTATACA 1810       1820       1830       1840       1850
    AGTTTTGAAATCTTATACATTATTATTGGGGAAAAACTTTTTAACCTGTT
    TCAAAACTTTAGAATATGTAATAATAACCCCTTTTTGAAAAATTGGACAA 1860       1870       1880       1890       1900
    CATTAAGGGCAACATCTTCTGCCTTAGCGCCTTTATTATCTACAAGATCA
    GTAATTCCCGTTGTAGAAGACGGAATCGCGGAAATAATAGATGTTCTAGT 1910       1920       1930       1940       1950
    TATTCTGCTACCATACTTTTCCACTCAATCTAATATCTAGCTGCGTCACC
    ATAAGACGATGGTATGAAAAGGTGAGTTAGATTATAGATCGACGCAGTGG 1960       1970       1980       1990       2000
    GTGCCCTTCAGCCAAAGCATGAAATGTGGGGCCAACCCTGCTTATCCTGC
    CACGGGAAGTCGGTTTCGTACTTTACACCCCGGTTGGGACGAATAGGACG 2010       2020       2030       2040       2050
    CAATTTACAGGGCTTTTGCCCAAACCGCATAAATAGTTCAATTAATTTCA
    GTTAAATGTCCCGAAAACGGGTTTGGCGTATTTATCAAGTTAATTAAAGT 2060       2070       2080       2090       2100
    AGAACCCAACCGACGCAGACTCTGTACAATGGAATTTGATTAAATTTATC
    TCTTGGGTTGGCTGCGTCTGAGACATGTTACCTTAAACTAATTTAAATAG 2110       2120       2130       2140       2150
    TTTAATTCTTCGACGCACCATTTTCAATTAAAATTGGGTACGGCAAACCA
    AAATTAAGAAGCTGCGTGGTAAAAGTTAATTTTAACCCATGCCGTTTGGT 2160       2170       2180       2190       2200
    TTTCTTACCAACCGCCAAGTGCAAGCTATGTAACTCCTTGATTGGTTATC
    AAAGAATGGTTGGCGGTTCACGTTCGATACATTGAGGAACTAACCAATAG
```

Fig. 9-5

```
         2210       2220       2230       2240       2250
TTATTTTAGATCAGGCTTTAGGGGTCTGTCGTAAAGAGACTTTACCACCT
AATAAAATCTAGTCCGAAATCCCCAGACAGCATTTCTCTGAAATGGTGGA 2260       2270       2280       2290       2300
CCAAATTCCCCACTGAACAAGCAATATGGAAAGGTGTCACATCCAAGAAT
GGTTTAAGGGGTGACTTGTTCGTTATACCTTTCCACAGTGTAGGTTCTTA 2310       2320       2330       2340       2350
CATCTGGATAATCGTCTGGAGTTAACATTTTCCATTTTGGAAAGCAAAAA
GTAGACCTATTAGCAGACCTCAATTGTAAAAGGTAAAACCTTTCGTTTTT 2360       2370       2380       2390       2400
ACTAGGTAATTTCATGTGCTTGGAAAGAAACTGATTAGTGTAAAGGGATT
TGATCCATTAAAGTACACGAACCTTTCTTTGACTAATCACATTTCCCTAA 2410       2420       2430       2440       2450
CTGCCATCCTAGTCCTTCTGTAGCAACAAGGAAGGTTTGGAGTGTAGCAG
GACGGTAGGATCAGGAAGACATCGTTGTTCCTTCCAAACCTCACATCGTC 2460       2470       2480       2490       2500
CTCTTGTACCTTGAAAAACTCATTTTCCATGCAGGCTTGATGCAAAGGAT
GAGAACATGGAACTTTTTGAGTAAAAGGTACGTCCGAACTACGTTTCCTA 2510       2520       2530       2540       2550
AATTAGACATGGTTATACAGTTTTAAGGGCATGCGTTTATCTAGTATTTT
TTAATCTGTACCAATATGTCAAAATTCCCGTACGCAAATAGATCATAAAA 2560       2570       2580       2590       2600
ATTATCACGCTTCAGCTGATCGTTCTTTAAAGAACCCTTTTATA
TAATAGTGCGAAGTCGACTAGCAAGAAATTTCTTGGGAAAATAT
```

PHO81 PROMOTOR OF SACCHAROMYCES CEREVISIAE AND USE THEREOF FOR HETEROLOGOUS GENE EXPRESSION

BACKGROUND OF THE INVENTION

1. Field of the Invention

This invention relates to a novel DNA construct, segment or fragment containing a promoter obtained from yeast and to an application thereof in genetic engineering.

2. Prior Art

With widespread utilization of recombinant DNA techniques, it has now become possible to produce useful polypeptides using prokaryotes or eukaryotes. *Escherichia coli* has thus far been employed in the large scale production of polypeptides. However, the use of eukaryotes is desired for the production of polypeptides particularly important in pharmacology. Yeasts, a group of eukaryotic microorganisms, have a number of similarities with mammalian cells and, therefore, are advantageous for use in the expression of genes coding for mammalian proteins. Further, yeasts do not contain endotoxin in their cells. Yeasts are easily cultivated. Culture of yeasts has been made from the past on a large, industrial scale, and its safety is confirmed. Additionally, a number of studies have been made to clarify their genetic biological mechanism. All the above circumstances surrounding yeasts have led to the utilization thereof as host organisms in genetic engineering.

Several yeast vectors for gene cloning are known at present. There are, however, few known yeast promoters capable of effectively expressing foreign genes.

Two acid phosphatases and two alkaline phosphatases are known to exist in a lysate of a strain of yeast *Saccharomyces cerevisiae*. The acid phosphatases are found on the surface of cells. The production of one of the acid phosphatases is suppressed by an inorganic phosphate, while the other acid phosphatase is constitutively produced. One of the alkaline phosphatases is a repressible one whose production is repressed by an inorganic phosphate and which has a wide substrate specificity. The other alkaline phosphatase is a specific p-nitrophenylphosphatase whose substrate is only p-nitrophenylphosphate, and which is constitutively produced. The mutants, pho5, pho4, pho2 and pho81 which lack repressible acid phosphatase activity have been isolated. The PHO5 gene is a structural gene for the repressible acid phosphatase, whereas the PHO4, PHO2 and PHO81 genes are genes which produce proteins regulating the expression of the repressible acid phosphatase structural gene PHO5. Further, the PHO4 and PHO81 genes serve to regulate the expression of repressive alkaline phosphatase structural gene similar to PHO5.

Various yeast vectors for gene cloning are known and may be utilized at present. In order to express native or endogeneous genes and foreign or exogeneous genes effectively, it is necessary to select a potent yeast promoter suitable for the host organisms to be used.

BRIEF DESCRIPTION OF THE DRAWINGS

FIG. 3 is a representation showing the identification of the PHO81 transcription products;

FIG. 5 shows the nucleotide sequence of the promoter region of the PHO81 gene;

FIGS. 9-1 to 9-5 show the DNA sequence containing the PHO81 gene.

SUMMARY OF THE INVENTION

Figure 1:
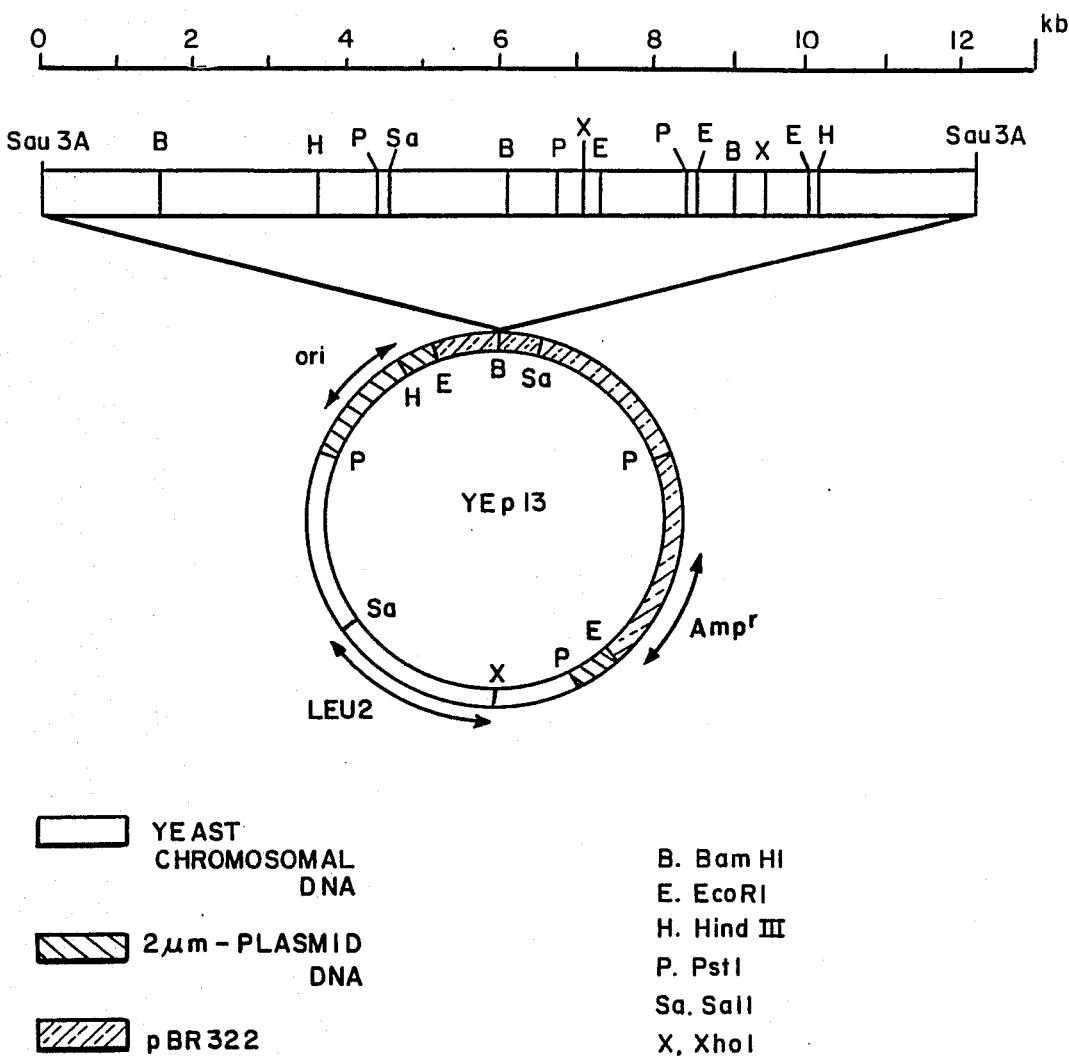
FIG. 1 is a restriction map of a plasmid pAC4 having an insertion of a DNA fragment bearing the PHO81 gene.

The present invention relates to a promoter of the PHO81 gene (hereinafter referred to as the PHO81 promoter). The PHO81 gene is a regulatory gene for expression of the structural genes of the repressible acid and alkaline phosphatases of yeast. Thus, the present inventors have cloned the PHO81 gene, determined the restriction enzyme cleavage map for the cloned DNA and determined the nucleotide sequence of the promoter region thereof. As a result, it has been found that the promoter is a novel DNA which may be suitably used for efficiently expressing both foreign and native genes. The present invention has been made on the basis of the foregoing studies.

More particularly, the present invention provides a DNA fragment having the promoter activity of the PHO81 gene regulating the production of phosphatase and being obtainable from *Saccharomyces cerevisiae;* a DNA fragment of the above-mentioned type, said fragment being a recombinant DNA; a DNA fragment bearing a structural gene coding for a positive regulatory factor for production of repressible phosphatases or other structural gene at a position downstream from the PHO81 promoter; a transformant containing a DNA fragment having a promoter activity of PHO81 gene regulating the production of phosphatase, and being obtainable from *Saccharomyces cerevisiae;* a transformant containing a DNA fragment bearing the above PHO81 promoter and a structural gene downstream from the PHO81 promoter; and a process for the production of a gene product including the steps of cultivating a transformant containing a DNA fragment having a promoter activity of PHO81 gene regulating the production of phosphatase, and being obtainable from *Saccharomyces cerevisiae* and a structural gene located downstream from said PHO81 promoter, so that the transformant grows with the accumulation of the gene product, and recovering the gene product from the culture. The above-described DNA fragment having a promoter activity of the PHO81 gene, the transcription of which is preferably regulated with phosphoric acid. The above-described DNA having a promoter activity of the PHO81 gene, is preferably, a DNA bearing a base sequence of between the position 1 and cleavage site with the restriction enzyme SmaI(CCC|GGG)
     (GGG|CCC)

in FIG. 9

DETAILED DESCRIPTION OF THE INVENTION

A DNA fragment, segment or construct according to the present invention containing the PHO81 promoter and a structural gene coding for the positive regulatory factor for the repressible phosphatase production (the PHO81 structural gene) may be isolated and collected from yeast cells.

Any strain of *Saccharomyces cerevisiae* may be used for this purpose. An especially suitable yeast strain is a strain of microorganism belonging to the genus Saccharomyces, such as *S. cerevisiae*. Commercially available baker's yeasts and brewer's yeast are particular examples of suitable yeast.

The extraction of DNA from yeast may be effected, for example, in accordance with the method described in Methods in Cell Biology, 12, 13–44 (1975).

The extracted DNA is treated with a suitable restriction enzyme to otain a DNA fragment. The fragment is ligated with a plasmid or phage which has been digested with the same restriction enzyme as above or with a restriction enzyme capable of forming the same or compatible cohesive ends as those with the above enzyme, thereby to obtain a gene bank. The plasmid may be, for example, pBR322 or *E. coli*-yeast shuttle vector YEp13 [Gene, 8, 121 (1979)]. The phage may be, for example, charon phage [J. Virol., 29, 555 (1979)]. If necessary, sub-cloning may be further effected with the use of, for example, *E. coli*-yeast shuttle vector YEp6 [Gene, 8, 17 (1979)].

A host organism is then transformed with the vector bearing the thus cloned DNA. The host organism is preferably yeast, particularly a strain belonging to the genus Saccharomyces, preferably a strain belonging to the species Saccharomyces cerevisiae, more particularly a strain of *Saccharomyces cerevisiae* NA95-4B. It is preferred that the host organism be a pho81 mutant.

The strain NA95-4B may be obtained by customarily employed crossing methods [Handbook of Genetics, p366, Plenum Press, New York (1974)]. That is, the strain NA95-4B may be obtained by crossing the strain AL211-12B (MATα, pho3-1, pho8, arg6) [Mol. Cell. Biol., 2, 127 (1982)], the strain AH22 (MATa, leu2, his4, canl) [Proc. Natl. Acad. Sci. USA, 80, 1 (1983)], the strain D13-1A (MATa, trpl, his3, gal2, SUC2) [Proc. Natl. Acad. Sci. USA, 76, 1035 (1979)], the strain YAT228 (MATa, leu2, lys10, cyh, karl-1) [J. Bacteriol., 145, 1421 (1981)] and the strain W755-1C (MATa, pho81, leu2, his3, his4).

The pho81 mutant is transformed with the DNA of the gene bank constructed as described above or subclone to obtain a plasmid containing the PHO81 structure gene bearing the PHO81 promoter and open reading frame coding for regulatory factor of the repressible phosphatase production.

The transformation may be performed in any known manner, for example, in accordance with one of the methods described in Proc. Natl. Acad. Sci. USA, 75, 1929 (1978), Nature, 275, 104 (1978), Cold Spring Harbor Symp., Quant. Biol., 43, 1305 (1979), and Proc. Natl. Acad. Sci. USA, 76 1035 (1979), or with the similar methods.

Whether or not the transformant contains the PHO81 promoter and the coding region of the PHO81 gene producing the regulatory factor for the repressible phosphatases can be determined in the following manner:

The transformant is cultured in Rubin's modified medium (C. M. Rubin, low phosphoric acid complete medium) [Eur. J. Biochem., 41, 197 (1974)] to allow for the formation of colonies. Then, the medium is overlaid with an agar layer containing α-naphthyl phosphate and fast blue salt B.

If the DNA containing the PHO81 promoter and the coding region of PHO81 protein, the regulatory factor for the repressible phosphatases, is cloned, the colonies will turn red, indicating the presence of the PHO81 gene. The plasmid is extracted from the transformant harboring the PHO81 gene and then digested with, for example, a restriction enzyme. The digest is then subjected to agarose gel electrophoresis or acrylamide gel electrophoresis to fractionate a DNA fragment having the inserted gene. A series of these operations is well known in the art and described in detail in, for example, Molecular Cloning (1982), Cold Spring Harbor Laboratory.

The nucleotide sequence of the DNA containing the PHO81 gene may be determined by, for example, the dideoxynucleotide synthetic chain termination method [Proc. Natl. Acad. Sci. USA, 74, 5463 (1977)], Maxam-Gilbert method [Proc. Natl. Acad. Sci. USA, 74, 560 (1970)] and so on.

Figure 2:
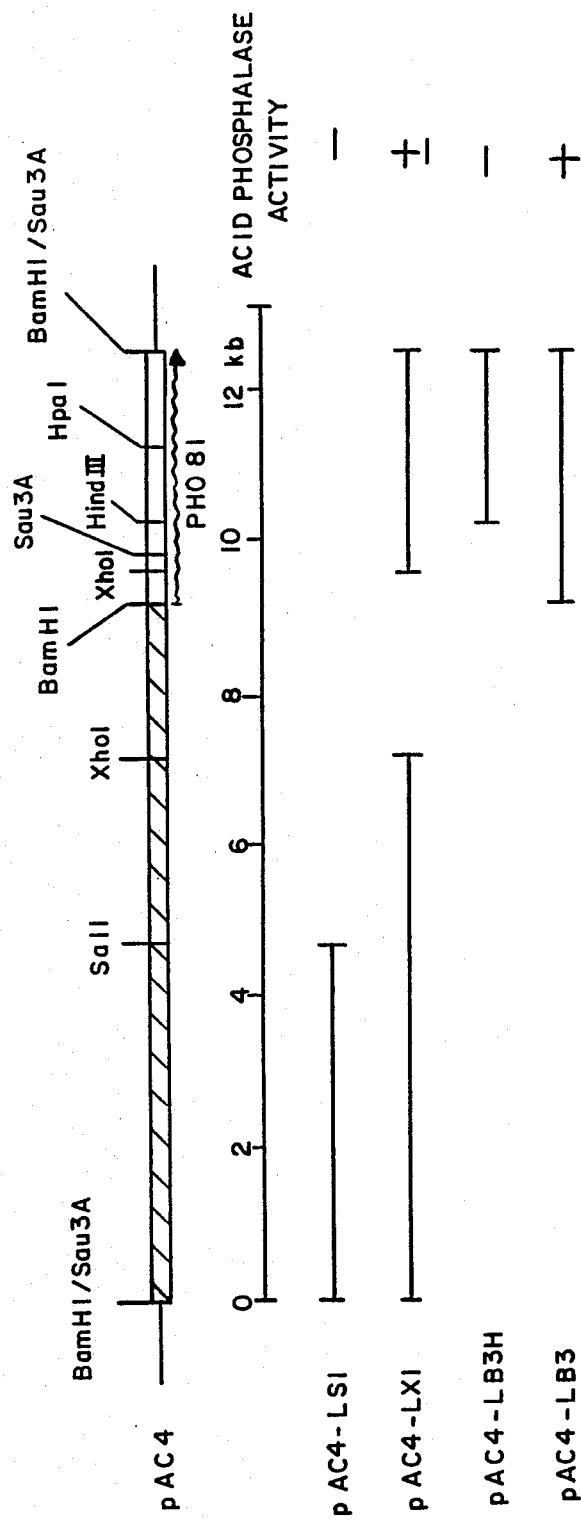
FIG. 2 is a schematic representation of restriction map for a DNA fragment and derivatives thereof bearing the PHO81 gene and the PHO81 promoter cloned according to the present invention, and indicating their ability to complement the PHO81 mutation.

The position of the protein-coding region of the PHO81 gene may be deduced by examining the relationship between deleted plasmids and their complementation ability of the pho81 mutation (FIG. 2). Using the plasmid bearing the suspected PHO81 gene (shown by white box in FIG. 2) as a probe, a PHO81 transcript is detected. From the size of the transcript and the base sequence of the PHO81 gene the position of the PHO81 promoter is estimated (FIGS. 3, 5 and 9).

Figure 7A:
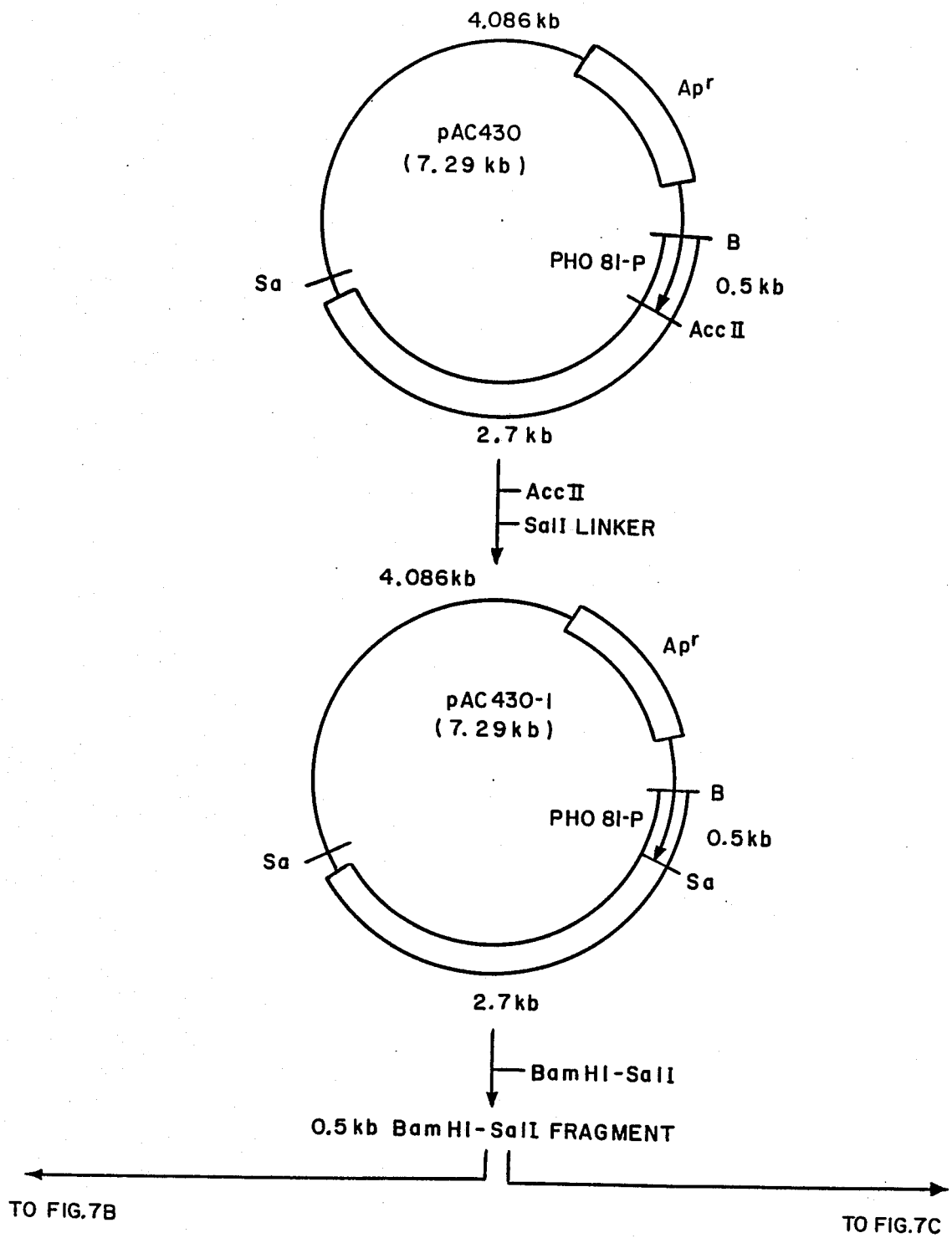
FIG. 7 is a scheme for constructing a recombinant DNA for the expression of adr type hepatitis B virus surface antigen gene.
Figure 7B:
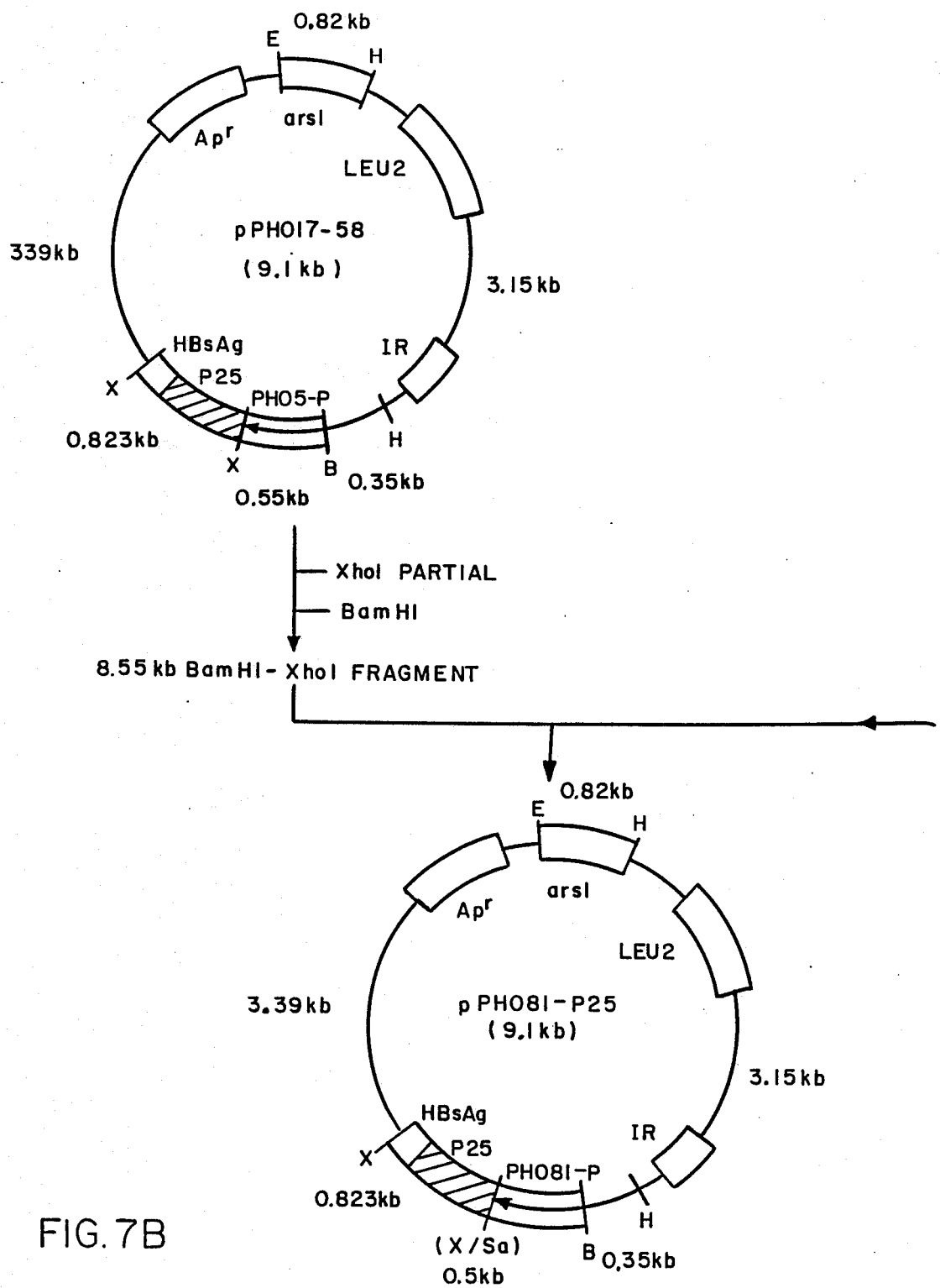
Figure 7C:
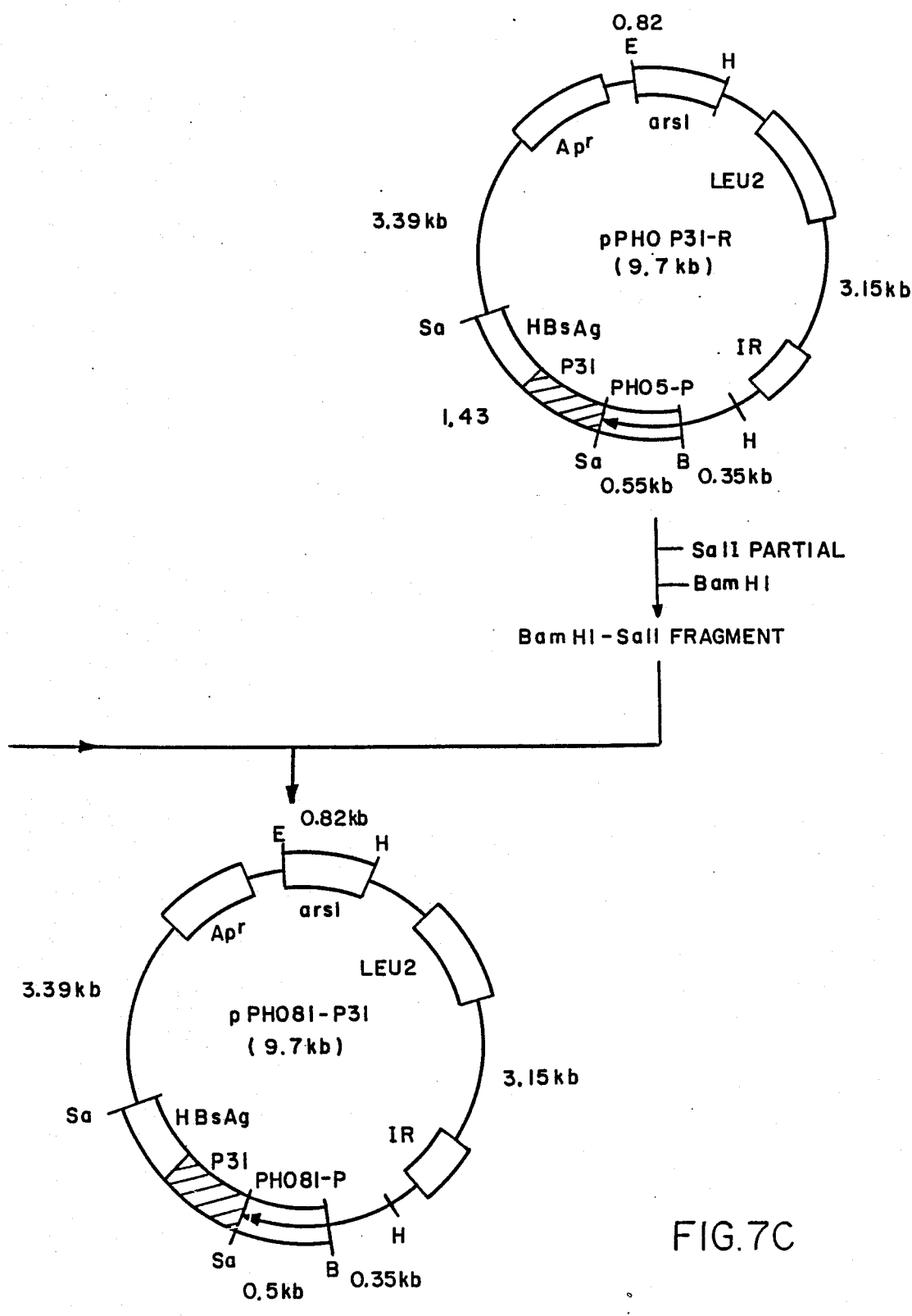
Figure 8:
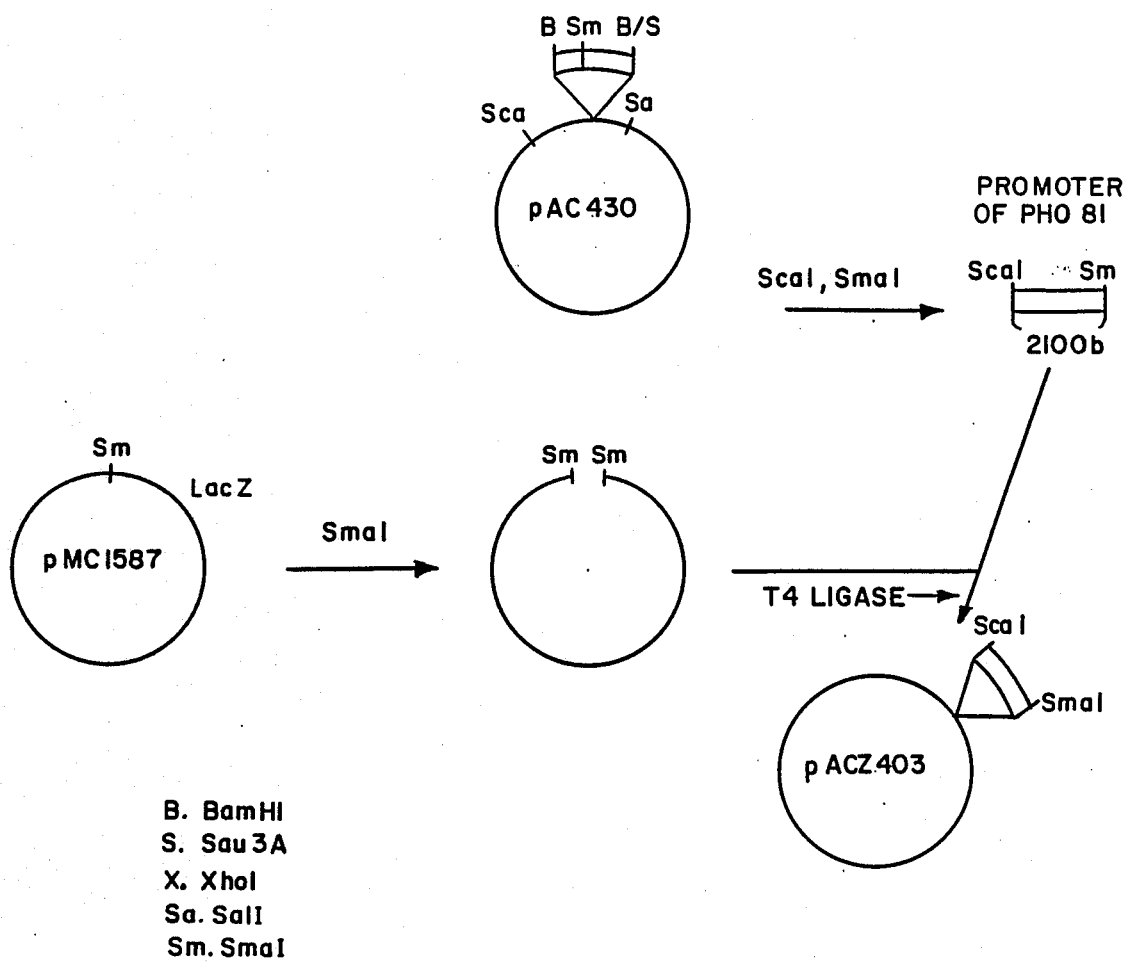
FIG. 8 is a a scheme for constructing a lacZ expression plasmid.

The base sequence of a region which is considered to contain the PHO81 promoter is then determined (FIG. 5). Determination of the nucleotide sequence indicates the presence of an open reading frame. The promoter is thus expected to locate upstream from the open reading frame. The portion of the DNA upstream from the open reading frame and having PHO81 promoter activity [ability to produce the regulatory factor for the repressible phosphatases production (See Table 1)] is prepared (FIG. 7). An expression vector is then prepared by inserting the portion having the PHO81 promoter activity and, if necessary, a desired structural gene downstream thereof into a vector (FIG. 8). The expression vector is inserted into a suitable host microbe which, upon culturing, produces the desired gene product.

The DNA bearing the PHO81 promoter activity may be entirely or partially synthesized by chemical processes and the synthetic or semisynthetic DNA may be used for the purpose of the present invention.

The vector into which the PHO81 promoter is inserted may be, for example, previously described shuttle vector YEp6 or YEp13 or plasmid pSH19 [Mol. Cell. Biol., 4, 771 (1984)] or pJDB219 [Nature, 275, 104 (1978)].

Illustrative of suitable structural genes to be inserted downstream from the PHO81 promoter are the regulating gene encoding the repressible acid phosphatase expression regulating factor (PHO81), the adw-type or adr-type hepatitis B virus surface antigen gene (HBsAg), human α-interferon gene, human β-interferon gene, human γ-interferon gene, human lisozyme gene, human interleukin-2 gene.

The host organism to be transformed with the PHO81 promoter-harboring DNA is preferably yeast, particularly a strain belonging to the genus Saccharomyces, preferably a strain belonging to the species S. cerevisiae, more particularly strains such as S. cerevisiae AH22R⁻ [Proc. Natl. Acad. Sci. USA, 80, 1 (1983)] or S. cerevisiae NA95-4B vide supra).

The transformants thus obtained may be cultured in any known medium such as Burkholder minimum medium [Proc. Natl. Acad. Sci. USA, 77, 4505 (1980)].

The culture conditions such as temperature and time may be varied so as to obtain the maximum yield of the desired gene product. Generally, a temperature of about 15°–40 °C., preferably about 24°–37° C. and a time of about 10–96 hours, preferably 24–72 hours are used. Aeration and agitation may be adopted, as necessary.

The gene product accumulated in the culture may be extracted in any known manner, such as by lyzing or disrupting the cells with the use of lysozyme such as Zymolyase (Seikagaku Kogyo, Ltd. Japan) or by mechanical disrupting method using glass beads. A detergent such as Triton-X100 and a protein denaturating agent such as guanidine hydrochloride may be used to facilitate the extraction of the product. The extract is then subjected to isolation and purification treatments conducted in conventional manner such as by precipitation using a precipitating agent, dialysis, electrophoresis, chromatography using ion exchange resins, gel filtration or a method using an antibody column.

In accordance with the present invention, there is provided a novel and potent promoter obtained from yeasts which are eukaryotic microorganisms. The promoter is very useful for the effective expression of pharmacologically important protein genes.

The following examples will further illustrate the present invention.

Saccharomyces cerevisiae P-28-24C used as a starting material in Example 1 is deposited at the Institute for Fermentation, Osaka, Japan under the accession number of IFO-10153, and deposited at the American Type Culture Collection (ATCC), U.S.A., under the accession number of ATCC 60202. The transformant S. cerevisiae P-28-24C. is deposited at IFO and ATCC under permanent deposition and is freely available to any requester.

The transformant, Escherichia coli DH1/pAC430 shown in Example 8 is deposited at the Institute for Fermentation, Osaka, Japan under the accession number of IFO-14456 and has also been deposited at Fermentation Research Institute, Agency of Industrial Science and Technology, Ministry of International Trade and Industry, Japan (FRI) under the accession number of FERM P-8411 since Aug. 9, 1985 and changed to the deposit under the accession number of FERM BP-1089 according to the Budapest Treaty.

The transformant, Saccharomyces cerevisiae AH22R⁻⁻ /pACZ403 shown in Example 12 is deposited at the Institute for Fermentation, Osaka, Japan under the accession number of IFO-10207 since May 28, 1986 and also deposited at FRI under the accession number of FERM BP-1090 according to the Budapest Treaty since June 25, 1986.

EXAMPLE 1

Cloning of the PHO81 gene (See FIG. 1)

Chromosomal DNA obtained in a conventional manner from S. cerevisiae P-28-24C (MATa pho3-1) (IFO 10153, ATCC 60202) was partially digested with Sau-3AI. The Sau3AI restriction fragments were inserted into the BamHI site of yeast-E. coli shuttle vector YEp13 [J. R. Broach et al., Gene, 8, 121 (1979)] according to the method of Nasmyth and Reed [K. A. Nasmyth & S. I. Reed, Proc. Natl. Acad. Sci. USA, 77, 2119 (1980)] to prepare a yeast gene bank consisting of about 2000 clones of E. coli showing the ampicillin resistant ($Amp^r$) and tetracycline sensitive ($Tc^s$) phenotype. The plasmid DNA of the yeast gene bank was introduced into the strain S. cerevisiae NA95-4B (MATα pho81 leu2 his3 trpl canl) for transformation. Transformants showing repressible acid phosphatase producing activity (rACp+) were screened by the colony staining method [modified method of G. Dorn, Genet. Res., 6, (1965)] using a 1% agar solution containing 0.5 mg/ml of α-naphthylphosphate, 5 mg/ml of fast blue salt B and 0.05M acetate buffer. Five rACp+ transformants were obtained from about $8 \times 10^3$ transformants which are prototrophic for leucine (Leu+). One of the five rACp+transformants was used to prepare a plasmid DNA according to the method of Cameron et al [J. R. Cameron et al., Nucleic Acids Res., 4, 1429 (1977)] and the plasmid DNA was transformed into E. coli JA221. All of the 35 $Amp^r$ transformants were $Tc^s$ and had a plasmid of the same molecular weight. This plasmid was named pAC4 and was again introduced into S. cerevisiae NA95-4B for transformation. Eighteen of the thus obtained Leu+ transformants were tested for their repressible acid phosphatase production activity to reveal that all of them were rACp+. This suggests that pAC4 has an insertion of a DNA fragment bearing the PHO81 gene. If PHO81 is included, then pAC4 is expected to be able to be integrated into the pho81 locus of chromosome by virtue of its homology. A stable transformant of S. cerevisiae YAT408 (leu2, lys10, canl, cir⁰) containing pAC4 was subjected to genetic analysis for the determination of the integration site of pAC4. Thus, the transformant containing pAC4 was crossed with S. cerevisiae YAT637 (MATa pho81 leu2) and was subjected to a tetrad analysis. As a result, the segregation of $Leu^{30}Acp^+$ and Leu⁻Acp⁻ phenotypes in tetrad showed 4:0, 3:1 and 2:2. The numbers of tetrads showing 4:0, 3:1 and 2:2 segregations were 0, 2 and 21, respectively. A second cross was carried out with the pAC4-containing transformant and S. cerevisiae YAT61 (MATa PHO81 LEU2). The tetrad analysis of the resultant diploid revealed that a ratio of the tetrads showing 4+:0−, 3+:1− and 2+:2− segregations of Leu phenotype was 2:33:4. The foregoing genetic data permit one to conclude that pAC4 is inserted on the PHO81 gene site or its vicinity, i.e., the PHO81 gene is cloned into pAC4.

EXAMPLE 2

Preparation of Restriction Enzyme Map for DNA Fragment Bearing the PHO81 Gene

The pAC4 DNA (1–5 μg) was digested in TA buffer [P. H. O'Farrell et al., Molec. Gen. Genet., 179, 421 (1980)] with 4–6 units of single or a combination of restriction enzymes selected from BamHI, EcoRI, HindIII, PstI, SalI and XhoI at 37° C. for 1 hour. The digestion products were electrophoresed on a 1% agarose gel or 7.5% polyacrylamide gel and the gels were examined for the restriction patterns to estimate molecular weights of the restriction fragments. Then, a restriction enzyme cleavage map was prepared as shown in FIG. 1, in which restriction sites are designated by letters as follows:

| E: | EcoRI | H: | HindIII |
|---|---|---|---|
| Sa: | SalI | X: | XhoI |
| P: | PstI | B: | BamHI |

EXAMPLE 3

Estimation of the Position of PHO81 Gene on Cloned DNA Fragment (See FIG. 2)

In order to estimate the position of the PHO81 gene in the cloned DNA fragment, various deletion derivatives of pAC4 were prepared. Thus, pAC4 (5 μg) was digested in 50 μl of TA buffer containing 6 units of BamHI at 37°C. for 1 min and then at 65° C. for 10 min to obtain a partially digested product. A 25 μl -portion of the digestion mixture was mixed with 50 μl of T4 ligase solution containing 5 mM MgCl$_2$, 10 mM dithiothreitol, 0.05 mM ATP and 3 units of T4 ligase and the mixture was allowed to stand at 4° C. for 18 hours to religate the partially digested product described above. E. coli JA221 was transformed with the use of the T4 ligase reaction solution (10 μl). From the Amp$^r$ transformants thus obtained, a plasmid DNA was isolated in accordance with the method of Birnboim and Doly [H. C. Birnboim & J. Doly, Nucleic Acids Res., 7, 1513 (1979)], to afford the deleted plasmid pAC4-LB3. The above procedures were repeated in the same manner using SalI and XhoI in place of BamHI to obtain pAC4-LS1 and pAC4-LX1, respectively. Further, pAC4-LB3 was treated in the same manner using HindIII to obtain the deleted plasmid pAC4-LB3H. Each of the resultant deleted plasmid DNA was used for transformation of S. cerevisiae NA95-4B and Leu+ transformants were selected. Ten selected transformant strains were tested for their phenotype with respect to repressible acid phosphatase (rACp+1). The positive or negative result of complementation tests of the pho81 mutation with the deletion plasmids is shown in FIG. 2 in terms of + and −.

S. cerevisiae NA95-4B was transformed with pAC4-LX1. The rACp producing activity of the resultant Leu+ transformants is lower than that of the wild type strain (the activity is shown as + in FIG. 2). The foregoing results indicate that the PHO81 gene is located at a region (about 3.0 kb) shown by the white box in FIG. 2.

EXAMPLE 4

Acid Phosphatase Producing Activity of Transformant Containing pAC4-LB3

The pAC4-LB3-containing transformant S. cerevisiae NA95-4B/pAC4-LB3 obtained in Example 3 was cultivated in 5 ml of Berkholder's modified high phosphoric acid medium and low phosphoric acid medium [A. Toh-e et al, J. Bacteriol., 113, 727 (1973)] for 20 hours with shaking. The cells were collected for measuring the acid phosphatase activity in accordance with the modified method of Torriani [A. Torriani, Biochim. Biophys. Acta, 38, 460 (1960)]. The results were as shown in Table 1.

As will be understood from Table 1, the production of the acid phosphatase by pAC4-LB3 is repressed by inorganic phosphate. Thus, the cloned PHO81 gene is considered to include both a region coding for the protein (PHO81 gene product) which regulates the expression of PHO5 and a promoter region.

TABLE 1

Acid Phosphatase Production Activity of Transformants Containing pAC4-LB3

| Strain of S. cerevisiae | Genotype a | Acid Phosphatase Activity* High Phosphoric Acid b | Low Phosphoric Acid c |
|---|---|---|---|
| P-28-24C | Wild type | 0.003 | 0.099 |
| NA95-4B/ pAC4-LB3 | pho81[pAC4-LB3] | 0.003 | 0.102 |
| NA95-4B | pho81 | 0.004 | 0.005 | a Indicated with respect to phosphatase only
*Units/ml/OD$_{660}$
b KH$_2$PO$_4$ concentration of 1.5 mg/ml
c KH$_2$PO$_4$ concentration of 0.03 mg/ml

EXAMPLE 5

Identification of PHO81 Gene Transcript

The transcription product of PHO81 was identified according to the Northern hybridization method. Total RNA was prepared from S. cerevisiae P-28-24C cultured in a complete medium (+P) and a low phosphoric acid medium (−P) in accordance with the method of Jensen [R. Jensen et al., Proc. Natl. Acad. Sci. USA, 80, 3035 (1983)], followed by purification by affinity column chromatography on oligo dT-cellulose in accordance with the method of Schleif and Wensink [R. F. Schleif & P. C. Wensink, Practical Methods in Molecular Biology, (1981), Springer-Verlag] to obtain poly(A)+RNA. The poly(A)+RNA sample thus obtained was subjected to formaldehyde gel electrophoresis as described in the article [Molecular Cloning, (1982), Cold Spring Harbor Laboratory], followed by blotting and hybridization according to the method of Thomas [P. S. Thomas, Proc. Natl. Acad. Sci. USA, 77, 5201 (1980)]. Autoradiography was performed at −80° C. employing a Kodak X-O-mat RP film and a Kodak intensifying screen. The probe DNA used for the identification of the transcript was prepared by nick translation [P. W. J. Rigby et al., J. Mol. Biol., 113, 237 (1977)] of a plasmid pAC450 obtained by subcloning a BamHI-SalI restriction fragment of about 3.2 kb, which was located between the BamHI restriction cleavage site in the vicinity of 9.2 kb of the cloned yeast chromosomal DNA (FIG. 1) and the SalI restriction cleavage site of YEp13, into pBR322 double-digested with BamHI and SalI.

The results are shown in FIG. 3. The size of the PHO81 transcript is 2.8 kb. The fact that the amount of the PHO81 transcript is much greater than that of the URA3 gene which codes for orotidine-5′-phosphate-decarboxylase [The Molecular Biology of the Yeast Saccharomyces, life cycle and inheritance, Cold Spring Harbor Lab., 731 (1981)] suggests the strong activity of the PHO81 promoter. Since the transcription of PHO81 is repressed in the high phosphate environment (+P), the PHO81 promoter is considered to be repressed by phosphoric acid.

EXAMPLE 6

Figure 4:
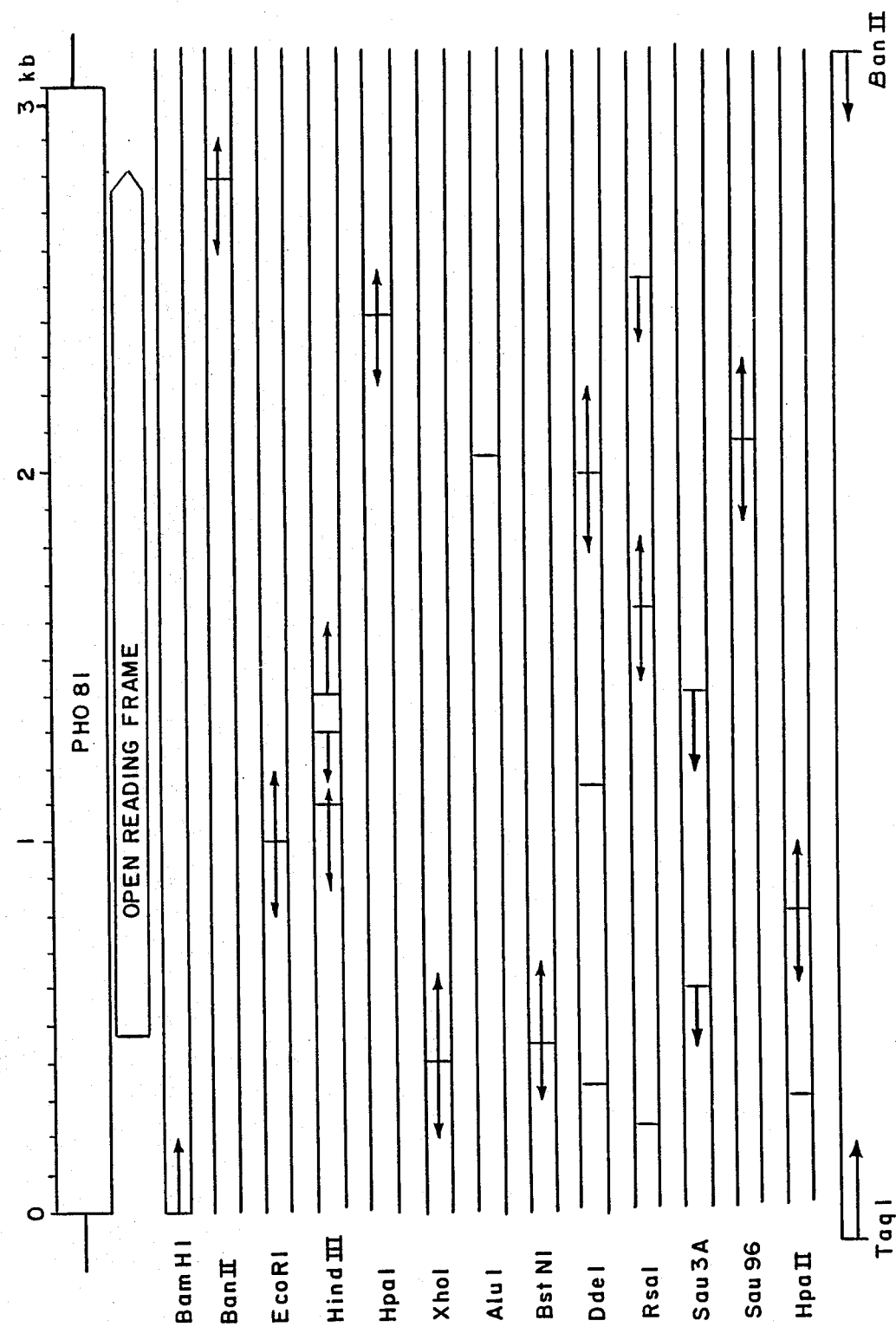
FIG. 4 illustrates cleavage maps for the base sequence of a cloned DNA fragment bearing PHO81.

Preparation of Restriction Enzyme Map for 3.0 kb DNA Fragment Bearing the PHO81 Gene The restriction enzyme map for the restriction fragment between the BamHI site and the Sau3AI/BamHI site including the PHO81 gene (the region shown by white box in FIG. 2) was prepared with the use of 14 different restriction enzymes (AluI, BanII, BstNI, DdeI, EcoRI, HaeIII, HindIII, HpaI, HpaII, RsaI, SalI, Sau3AI, Sau96I and XhoI) and is shown in FIG. 4. The fragment was digested with one or a combination of two of the enzymes. The digestion mixtures were electrophoresed on 7.5% or 12% polyacrylamide gels. Restriction enzyme cleavage sites were estimated from the cleavage patterns. A HaeIII or AluI digest of pBR322 was used as a molecular weight marker. Only the restriction enzyme cleavage sites whose positions are confirmed are shown in FIG. 4.

EXAMPLE 7

Determnation of the Base Sequence of DNA Bearing the PHO 81 Gene

The base sequence of the DNA fragment of 3.0 kb located between BamHI and BamHI/Sau3A sites (See FIG. 2) and considered to bear the PHO81 gene was determined according to the method of Maxam and Gilbert (vide supra) and is shown in FIG. 5. In the nucleotide sequence, there exists a translatable region of about 2.5 kb. From this frame, the direction of transcription is expected to be from the BamHI site to the BamHI/Sau3A site. A translational initiation codon "ATG" is present at about 520 bases downstream from the BamHI cleavage site. At 67 bp (base pairs) upstream from the "ATG", there is present a sequence TATTA which is considered to function as a TATA box. A sequence TCATCA, which is similar to capping site, exists at 57 bp upstream from the "ATG". Further, there is a sequence CCAAT at 109 bp upstream from the "ATG". This sequence is identical with that of CCAAT box [Nucleic Acids Res., 10, 2625-2637 (1982); ibid 12, 857-872 (1984); ibid 12, 1137-1148 (1984)]. FIG. 5 shows the base sequence of a region of 700 bases downstream from the BamHI cleavage site. A non-translational region of 5'-upstream side of the PHO81 gene and a 5'-terminal region of the PHO81 gene are considered to be included within the illustrated region.

EXAMPLE 8

Construction of Plasmid pAC430 and Preparation of Transformant Using Same

Figure 6:
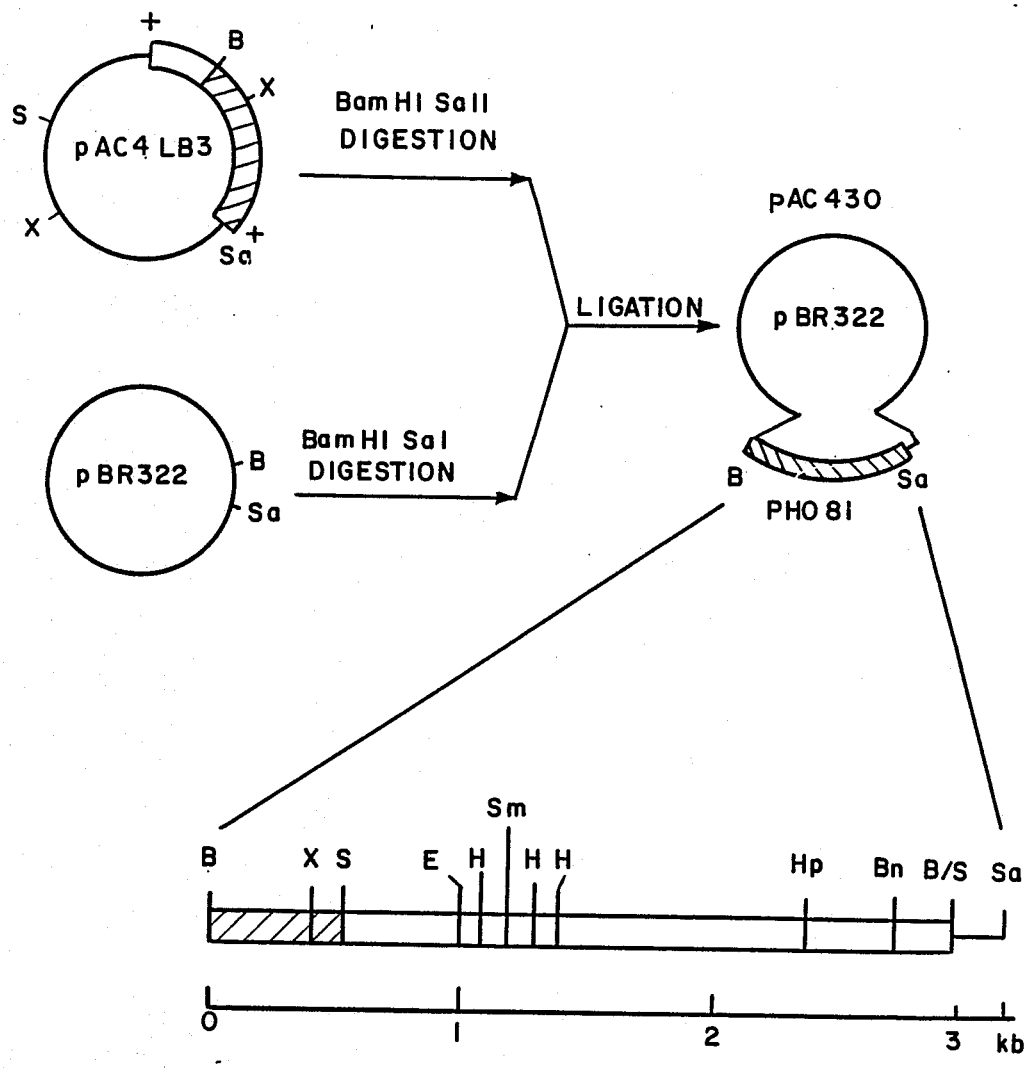
FIG. 6 is a scheme for constructing the pAC430 plasmid.

The plasmid pAC4-LB3 (5 μg) was digested with 5 units of BamHI and 5 units of SalI in the manner described in Example 2. The digestion mixture was subjected to electrophoresis on a 1% low melting agarose gel to recover a DNA fragment of 3.2 kb. This fragment was mixed with pBR322 (5 μg) digested with 5 units of BamHI and 5 units of SalI, and the mixture was ligated by T4 ligase in the same manner as described in Example 2 to obtain a plasmid pAC430 (See FIG. 6). The plasmid pAC430 was introduced into E. coli DH1 for transformation to obtain a transformant Escherichia coli DH1/pAC430(IFO 14456, FERM BP-1089).

EXAMPLE 9

Construction of adw-Type Hepatitis B Virus Surface Antigen P25 Gene Expression Plasmid Using the PHO81 Promoter and Transformation of Yeast with the Plasmid The plasmid pAC430 (0.5 μg) is digested with 1 unit of restriction enzyme AccII (manufactured by Nippon Gene Inc.) in 20 μl of a reaction medium [6 mM Tris-HCl (pH7.5), 60 mM NaCl, 6 mM MgCl$_2$, 6 mM 2-mercaptoethanol] at 37° C. for 2 hours, followed by elimination of protein with phenol and the DNAs were precipitated by addition of cold ethanol. The precipitated DNA is mixed with 50 ng of a SalI linker having a phosphorylated 5'-terminal [5'-P-d(GGTCGACC)] (manufactured by New England Biolabs Inc.) and the mixture was reacted in 20 μl of a reaction liquid containing 66 mM Tris-HCl (pH7.6), 6.6 mM MgCl$_2$, 10 mM dithiothreitol, 1 mM ATP and 2 units of T4 DNA ligase (manufactured by New England Biolabs. Inc.) at 14° C. overnight to ligate the DNA. E. coli DH1 [T. Maniatis et al., Molecular Cloning, Cold Spring Harbor Laboratory, 254–255 (1982)] is transformed with the use of the above ligation liquid, and ampicillin resistant transformants were selected. From the selected transformants, plasmid pAC430-1 having a SalI site substituted for the AccII site of the plasmid pAC430 is obtained (See FIG. 7). The plasmid pAC430-1 (10 μg) is digested with 10 units of restriction enzyme BamHI and 10 units of restriction enzyme SalI (manufactured by Nippon Gene Inc.) in 50 μl of a reaction medium [10 mM Tris-HCl (pH7.5), 7 mM MgCl$_2$, 100 mM NaCl, 7 mM 2-mercaptoethanol] at 37° C. for 2 hours. The digest is then applied to a 1.2% agarose-slab gel and electrophoresed in a buffer [100 mM Tris-HCl, 100 mM boric acid, 2 mM EDTA (pH 8.3)] at 140 V for 2 hours. After the electrophoresis, the region of the gel containing 0.5 kb DNA fragment is placed in a dialysis tube and immersed in the above electrophoresis buffer. The DNA fragment is extracted from the gel by electrical elution [M. W. McDonell et al., J. Mol. Biol., 110, 119 (1977)]. The liquid within the dialysis tube is extracted with phenol and then with ether. Following extraction, the aqueous phase is adjusted to 0.2M with NaCl. The DNA fragment containing the PHO81 promoter is precipitated by the addition of 2 volumes of cold ethanol.

The adw-type hepatitis B virus surface antigen (HBsAg P25) gene expression plasmid pPHO17-58 (50 μg) disclosed in the Example of the specification of Japanese-Patent Application No. 59-193765 filed Sept. 13, 1984 (which corresponds to European Patent Publication No. 175283 and corresponds pending U.S. patent Appln. Ser. No. 774,333 filed September 10, 1985) is partially digested with 50 units of restriction enzyme XhoI (manufactured by Nippon Gene Inc.) in 100 μl of a reaction medium [10 mM Tris-HCl (pH 7.5), 7 mM MgCl$_2$, 100 mM NaCl, 7 mM 2-mercapto- ethanol] at 37° C. for 20 min. From the digest mixture is separated a DNA fragment of 9.1 kb, which is cleaved at only one of the two XhoI restriction enzyme cleavage sites of the plasmid, by means of the agarose-slab gel under the same condition as described previously.

The DNA fragment of 9.1 kb (4 μg) thus recovered is then digested with 4 units of restriction enzyme BamHI in 20 μl of a reaction medium [6 mM Tris-HCl (pH 7.9), 150 mM NaCl, 6 mM MgCl$_2$] at 37° C. for 2 hours, followed by electrophoresis conducted under the same conditions as above, thereby to isolate 8.55 Kb DNA.

The 8.55 kb DNA (200 ng) is ligated with the 0.5 kb DNA (20 ng) containing the PHO81 promoter using T4 DNA ligase. With the use of the resultant mixture, *E. coli* DH1 is transformed. From the ampicillin resistant transformants, transformant DH1/pPHO81-P25 containing the plasmid pPHO81-P25 in which the PHO81 promoter is inserted in the same direction as the HBsAgP25 gene is selected. Plasmid pPHO81-P25 is then isolated from the transformant (See FIG. 7) and introduced into a yeast strain of *Saccharomyces cerevisiae* AH22R−, thereby to obtain transformant AH22R−/pPHO81-P25.

EXAMPLE 10

Construction of an Expression plasmid for the production of adr-type Hepatitis B Virus Surface Antigen P31 Using PHO81 Promoter and Transformation of Yeast with the Plasmid The adr-type hepatitis B Virus surface antigen (HBsAg P31) gene expression plasmid pPHO P31-R (50 μg) disclosed in Example 3 of International Patent Application No. PCT/JP84/423 (International Filing Date: September 4, 1984) (which corresponds to European Patent Publication No.171908 and corresponds to pending U.S. patent application Ser. No. 753,540 filed Jul. 10, 1985) is digested with 50 units of restriction enzyme SalI in 100 μl of a reaction medium [6 mM Tris-HCl (pH 7.9), 150 mM NaCl, 6 mM MgCl$_2$, 6 mM 2-mercaptoethanol] at 37°C. for 20 min. From the digest is separated a DNA fragment of 9.7 kb, which is cleaved at only one of the two SalI restriction enzyme cleavage sites of the plasmid, by means of the agarose-slab gel in the same manner as above.

The DNA fragment of 9.7 kb (4 μg) thus recovered is then digested with 4 units of restriction enzyme BamHI, followed by electrophoresis under the same conditions as above, thereby to isolate a 9.2 kb DNA. The 9.2 kb DNA (200 ng) is ligated with the 0.5 kb DNA (20 ng) containing the PHO81 promoter with the employment of T4 DNA ligase. Using the resultant mixture, *E. coli* DH1 is tansformed. From the ampicillin resistant transformants, transformant DH1/pPHO81-P31 containing the plasmid pPHO81-P31 in which the PHO81 promoter is inserted in the right direction as the HBsAg P31 gene is selected. Plasmid pPHO81-P31 is then isolated from the transformant (See FIG. 7) and introduced into yeast host *Saccharomyces cerevisiae* AH22R− to obtain transformant AH22R−/pPHO81-P31.

EXAMPLE 11

Expression of the HBsAg Gene in Yeast

The transformants *Saccharomyces cerevisiae* AH22R−/pPHO81-P25 and AH22R−/pPHO81-P31 containing the HBsAg gene expression plasmid and obtainable in Examples 9 and 10 are cultivated at 30° C. for 2 days in Burkholder medium and its low phosphoric acid medium. Cells are collected and washed with physiological saline solution. The cells are then treated with Zymolyase (Seikagaku Kogyo Co. Ltd., Japan) in accordance with the method of Miyanohara [A. Miyanohara, Proc. Natl. Acad. Sci. USA, 80, 1 (1983)] to form spheroplasts. After adding 0.1% of Triton X-100 for expediting extraction of HBsAg, the lysate is centrifuged at 15,000 rpm for 15 min at room temperature. The supernatant liquid was tested for the detection of HBsAg activity by means of Orthzyme II (manufactured by Dynabot K. K.).

EXAMPLE 12

Expression of lacZ Gene Using PHO81 Promoter

Using respectively 10 units of restriction enzyme ScaI and SmaI (manufactured by Takara Shuzo Co. Ltd., Japan), 10 μg of pAC430 containing PHO81 gene (the region from the white box portion in FIG. 2 to the SalI site of YEp13) were digested in 100 μl of a reaction medium [33 mM Tris-acetic acid (pH7.9), 66 mM K-acetate, 10 mM Mg-acetate, 5 mM dithiothreitol] at 37° C. for 2 hours. The digest was applied to a 4% acrylamide gel and electrophoresed in buffer (89 mM Tris, 89 mM boric acid, 2.5 mM EDTA) at 150 V for 3 hours. Following the electrophoresis, the portion of the gel containing 2100 bp DNA fragment (ScaI-SmaI restriction fragment) was placed in a Corex tube for the destruction thereof, to which was then added 5 ml of a DNA extraction buffer of 0.5M (NH$_4$)COOCH$_3$, 10 mM Mg-acetate, 1 mM EDTA, 0.1% (w/v) SDS. The resultant mixture was allowed to stand overnight at 37° C. and filtered. The DNA fragment was precipitated by the addition of ethanol to the filtrate and recovered for use in the ligation reaction described below.

Plasmid pMC1587 (1 μg) was digested with 1 unit of restriction enzyme SmaI (manufactured by Takara Shuzo Co. Ltd.) in 50 μl of a reaction mixture (1 mM Tris, 10 mM NaCl, 0.6 mM MgCl$_2$) at 37° C. for 2 hours. The restriction DNA fragment was precipitated with ethanol and recovered. The above described DNA fragment (0.1 μg) from pMC1587 digested with SmaI was ligated with the ScaI-SmaI restriction fragment of 2100 bp(5 μg) using T4 DNA ligase to produce a plasmid pACZ403(FIG. 8). In the thus obtained plasmid, a portion of the PHO81 translational sequence located in the ScaI-SmaI DNA fragment of 2100 bp was ligated at the SmaI connecting site with the lacZ translational sequence located in the pMC1587, with the reading frames of both genes being ajusted.

The thus obtained plasmid pACZ403 was introduced into *Saccharomyces cerevisiae* AH22R− to obtain transformant *Saccharomyces cerevisiae* AH22R−/pACZ40-3(IFO-10207, FERM BP-1090). The transformant was cultured for 20 hours in the same manner as described in Example 11 and the cells were treated in the same manner as described in Example 11 to obtain the following results.

| | The expression of β-galactosidase unit/l |
|---|---|
| The medium containing high concentration of phosphoric acid (KH$_2$PO$_4$ 1.5 g/l) | 600 |
| The medium containing low concentration of phosphoric acid (KH$_2$PO$_4$ 0.3 g/l) | 2600 |

EXAMPLE 13

Sequencing of PHO81 Gene

The DNA sequence of the BamHI-BanII fragment (about 2.6 kb) containing the PHO81 gene was determined according to the method of Maxam and Gilbert described in Example 7 and is shown in FIG. 9. In the base sequence, there exists a "stop codon" at about 2330 bp region.

The following references, which are referred to for their disclosures at various points in this application, are incorporated herein by reference.

Methods in Cell Biology, 12, 13–44(1975).
Gene, 8, 121 (1979).
J. Virol., 29, 555 (1979)
Gene, 8, 17 (1979).
Handbook of Genetics, p366, Plenum Press, New York(1974).
Mol. Cell. Biol., 2, 127 (1982).
Proc. Natl. Acad. Sci. USA, 80, 1 (1983).
Proc. Natl. Acad. Sci. USA, 76, 1035 (1979).
J. Bacteriol., 145, 1421 (1981).
Proc. Natl. Acad. Sci. USA, 75, 1929 (1978).
Nature, 275, 104 (1979).
Eur. J. Biochem., 41, 197 (1974).
Proc. Natl. Acad. Sci. USA, 74, 5463 (1977).
Proc. Natl. Acad. Sci. USA, 74, 560 (1970).
Mol. Cell. Biol., 4, 771 (1984).
Nature, 275, 104 (1978).
Proc. Natl. Acad. Sci. USA, 80, 1 (1983)
Proc. Natl. Acad. Sci. USA, 77, 4505 (1980).
Gene, 8, 121 (1979).
Proc. Natl. Acad. Sci. USA, 77, 2119 (1980)
Genet. Res., 6, (1965).
Nucleic Acids Res., 4, 1429 (1977).
Molec. Gen. Genet., 179, 421 (1980).
Nucleic Acids Res., 7, 1513 (1979).
J. Bacteriol., 113, 727 (1973).
Biochim. Biophys. Acta, 38, 460 (1960).
Proc. Natl. Acad. Sci. USA, 80, 3035 (1983).
Practical Methods in Molecular Biology, (1981). Springer-Verlag.
Proc. Natl. Acad. Sci. USA, 77, 5201 (1980).
J. Mol. Biol., 113, 237 (1977).
The Molecular Biology of the Yeast Saccharomyces, Life Cycle and Inheritance, Cold Spring Harbor Lab., 731 (1981).
Nucleic Acids Res., 10, 2625–2637 (1982). ibid 12, 857–872 (1984); ibid 12, 1137–1148(1984).
Molecular Cloning, Cold Spring Harbor Laboratory, 254–255 (1982).
J. Mol. Biol., 110, 119 (1977).

What is claimed is:

1. A recombinant DNA fragment which comprises the *Saccharomyces cerevisiae* PHO81 promoter, which DNA fragment when operably linked to a structural gene is capable of regulating the transcription thereof.

2. A hybrid plasmid which comprises the recombinant DNA fragment of claim 1.

3. The DNA fragment of claim 1 wherein the PHO81 promotor is operably linked to a structural gene.

4. The DNA fragment of claim 3, wherein the structural gene is one other than that coding for a positive regulatory factor for production of repressible phosphatases.

5. The DNA fragment of claim 4, wherein the structural gene is selected from the group consisting of the adw-type hepatitis B virus surface antigen P25 gene, the adr-type hepatitis B virus surface antigen P31 gene and the lacZ gene.

6. A microorganism which has been transformed with a hybrid plasmid comprising the *Saccharomyces cerevisiae* PHO81 promotor.

7. The transformed microorganism of claim 6, wherein the PHO81 promotor is operably linked to a heterologous structural gene.

8. The transformed microorganism of claim 6 which is *Escherichia coli* DH/pAC430.

9. The transformed microorganism of claim 6 wherein the transformed microorganism is a yeast.

10. The transformed microorganism of claim 9 which is *Saccharomyces cerevisiae* AH22R⁻/pPHO81-P25.

11. The transformed microorganism of claim 9 which is *Saccharomyces cerevisiae* AH22R⁻/pPHO81-P31.

12. The transformed microorganism of claim 9 which is *Saccharomyces cerevisiae* AH22R⁻/pACZ403.

13. A process for the producing a heterologous polypeptide from *Saccharomyces cerevisiae* said process comprising:

(1) transforming a *Saccharomyces cerevisiae* host strain with a hybrid plasmid which comprises the *Saccharomyces cerevisiae* PHO81 promotor operably linked to a heterologous gene which codes for a heterologous polypeptide;
    (2) culturing the transformed *Saccharomyces cerevisiae* host strain under conditions suitable for expression of the heterologous polypeptide, and;
    (3) recovering the expressed heterologous polypeptide from the culture medium.

14. The process of claim 13 wherein the level of transcription is controlled by adjusting the amount of phosphoric acid in the culture medium.

* * * * *